United States Patent [19]

Urbas

[11] 4,405,717

[45] Sep. 20, 1983

[54] RECOVERY OF ACETIC ACID FROM A FERMENTATION BROTH

[75] Inventor: Branko Urbas, Darien, Ill.

[73] Assignee: CPC International Inc., Englewood Cliffs, N.J.

[21] Appl. No.: 314,627

[22] Filed: Oct. 26, 1981

[51] Int. Cl.$^3$ .................... C07C 51/48; C07C 51/50; C12P 7/54

[52] U.S. Cl. .................... 435/140; 435/842; 203/16; 203/38; 562/513; 562/608

[58] Field of Search .............. 435/140, 141, 842; 426/17; 562/513, 608; 203/16, 43, 59, 38, 33; 159/47 R

[56] References Cited

U.S. PATENT DOCUMENTS

| | | | |
|---|---|---|---|
| 1,864,838 | 6/1932 | Langwell et al. | 435/140 |
| 3,158,649 | 11/1964 | Colin et al. | 562/513 |
| 3,238,252 | 3/1966 | Giacometti | 562/513 |
| 3,816,524 | 6/1974 | Grinstead | 562/513 |
| 4,100,189 | 7/1978 | Mercier | 562/608 |
| 4,282,323 | 8/1981 | Yates | 435/140 |
| 4,364,960 | 12/1982 | Kunimatsu et al. | 435/140 |
| 4,371,619 | 2/1983 | Schwartz et al. | 435/140 |

FOREIGN PATENT DOCUMENTS 1426018  2/1976  United Kingdom .

OTHER PUBLICATIONS

Wardell et al.: Journal of Chemical Eng. Data, vol. 23, No. 2, 1978, *Solvent Equilibra for Extraction of Carbon Acid from Water.*

*Primary Examiner*—Wilbur L. Bascomb, Jr.
*Attorney, Agent, or Firm*—Stanley M. Parmerter

[57] ABSTRACT

A process is provided for the recovery of acetic acid from dilute aqueous solutions. The acid in the form of its calcium salt is treated with a tertiary amine carbonate and the resulting trialkylammonium acetate is isolated and heated to give the acetic acid plus a tertiary amine.

20 Claims, No Drawings

RECOVERY OF ACETIC ACID FROM A FERMENTATION BROTH

FIELD OF THE INVENTION

This invention relates to a method for the extraction of acetic acid from a dilute aqueous solution in which the acetic acid is present in the form of its calcium salt.

BACKGROUND OF THE INVENTION

The production of acetic acid by microorganisms is well known to those familiar with the fermentation art. This acetic acid is produced by the microorganisms in dilute aqueous solutions so that its recovery in pure form involves separation from a large quantity of water. The expense of such separation has been so great that the production of acetic acid by fermentation has not been able to compete with the production of acetic acid based on petroleum fossil fuel sources. However, the gradual depletion of petroleum fossil fuel with the resultant increase in prices of petrochemical feedstocks has revived interest in such fermentation reactions which can convert carbohydrates that are renewable raw materials into acetic acid and other simple organic chemicals.

When acetic acid is made by fermentation, the acid formed soon lowers the pH of the medium to a point at which the microorganism no longer grows, and acid production eventually stops. For this reason, it is necessary to add a reagent to the fermentation reaction which will neutralize at least a part of the acetic acid and maintain the pH at a high enough level to permit continued growth of the microbe. The solution must then be acidified before the acetic acid is extracted. The neutralization and acidification steps add to the cost of the process and produce salts which must be disposed of.

It would be of considerable economic importance if a low-cost process could be developed for the extraction of acetic acid produced by such fermentation reactions. It would be an added benefit if the reagent needed to adjust the pH in the fermentation reaction could be recovered for reuse in the process.

Daniel, et al., in British Pat. No. 1,426,018, published Feb. 25, 1976, disclose a process for the recovery of an acid from an aqueous solution. The extractant is a mixture of an amine which contains at least 20 carbon atoms per molecule and a water-immiscible organic solvent. In order to obtain the acid, it is necessary to back-extract the acid from the organic solvent with water. The resultant solution still contains a large percentage of water and only a partial concentration of the acid is accomplished by this procedure.

A recent review of the methods of extraction of acetic acid from water is given by C. J. King in the proceedings of the International Solvent Extraction Conference, Series 2, Paper 80-66 (1980). This review includes a summary of the following three references which report work carried out in King's laboratory:

Wardell, et al., J. Chem. Eng. Data, 23, 144 (1978).
Ricker, et al., J. Separ. Proc. Technol., 1 (1) 36–41 (1979).
Ricker, et al., J. Separ. Proc. Technol., 1 (2) 23-33 (1980).

King discloses the extraction of acetic acid from dilute aqueous solutions using various solvent systems. The best solvent systems were mixtures of a high molecular weight tertiary amine or a trialkyl phosphine oxide diluted with a polar solvent. The preferred solvent was a mixture of a commercial amine, consisting largely of trioctylamine, and diisopropyl ketone. The use of tributylamine was dismissed because the tributylamine-acetic acid complex was too soluble in water for this amine to be satisfactory for the extraction.

A convenient method for the extraction of acetic acid has now been discovered. This process does not require prior acidification of the fermentation broth and permits the use of solvents previously considered to be unsuitable for the extraction. Furthermore, the reagent needed for maintaining the pH in the fermentation broth is recovered for reuse in the process.

SUMMARY OF THE INVENTION

In accordance with the present invention, there is provided a process for the recovery of acetic acid from a fermentation reaction which comprises:

(a) converting of the acetic acid to calcium acetate;

(b) adding a molar equivalent of a water-soluble tertiary amine carbonate to the calcium acetate solution to form a trialkylammonium acetate solution and a precipitate of calcium carbonate;

(c) concentrating the trialkylammonium acetate solution; and (d) heating the concentrated trialkylammonium acetate solution to obtain acetic acid and the tertiary amine.

Also, in accordance with the invention, there is provided a process for the recovery of acetic acid from an aqueous solution of calcium acetate which comprises the steps of:

(a) adding a molar equivalent of a water-soluble tertiary amine carbonate to the calcium acetate solution to form a trialkylammonium acetate solution and a precipitate of calcium carbonate;

(b) concentrating the trialkylammonium acetate solution; and (c) heating the concentrated trialkylammonium acetate solution to obtain acetic acid and the tertiary amine.

DETAILED DESCRIPTION OF THE INVENTION

The process of this invention can be used to extract acetic acid from any dilute solution of the acid. It is particularly suitable for extraction of acetic acid from solutions which contain the acetic acid in the form of its calcium salt. Such solutions are obtained from acetic acid-producing fermentation reactions in which the pH is maintained in the range of from about 4.5 to about 7.0 by the addition of calcium carbonate or calcium hydroxide. The concentration of acetic acid, or calcium acetate, in the solution can vary over a wide range, but is usually less than about 10% by weight.

In carrying out the process of this invention, a molar equivalent of a water-soluble tertiary amine carbonate is added to the calcium acetate solution. The tertiary amine carbonate used in the process can be generated by the addition of carbon dioxide to a solution or suspension of the tertiary amine in water. It is most convenient to generate the tertiary amine carbonate in situ by first adding a molar equivalent of the tertiary amine to the calcium acetate solution. Then carbon dioxide is added to the mixture to generate the tertiary amine carbonate directly in the calcium acetate solution. The addition of the carbon dioxide is carried out by any convenient means. Either solid or gaseous carbon dioxide is added to the solution at atmospheric pressure or at higher pressures in a pressure vessel.

The amines used in the process of this invention are preferably tertiary amines. Primary and secondary amines tend to form amides with acetic acid under the conditions of the process, and for this reason, are less satisfactory. Any tertiary amine which forms a water-soluble carbonate with carbon dioxide under the conditions of the process can be used. Preferred amines are those which do not form azeotropes with acetic acid and which distill at a temperature sufficiently above that of the distillation temperature of acetic acid to permit separation of acetic acid from a mixture of acetic acid and the amine by fractional distillation. The amine should be sufficiently stable on heating so that it does not undergo decomposition when the trialkylammonium acetate is heated in the final step of the process.

The lower molecular weight tertiary amines, trimethylamine, triethylamine and tripropylamine, form carbonates which are water soluble. However, these amines either form azeotropes with acetic acid or tend to codistill with acetic acid. The higher symmetrical amines, such as trihexylamine and trioctylamine, do not form carbonates which are sufficiently soluble in water. Higher molecular weight tertiary amines, in which one of the alkyl groups is methyl or ethyl, do form water-soluble carbonates, but they tend to undergo decomposition when heated to a temperature sufficient to decompose their acetates in the last step of the process.

The tertiary amines, dicyclohexylmethylamine and tributylamine, are suitable for use in this process. Tributylamine is preferred. This amine dissolves readily when carbon dioxide is added to a mixture of the amine in a dilute calcium acetate solution. Furthermore, tertiary butylamine has a sufficiently high boiling point so that it does not distill at a temperature of about 160°–180° C., the temperature at which tributylammonium acetate readily dissociates with acetic acid distilling from the mixture.

When a water-soluble tertiary amine carbonate is mixed with the calcium acetate solution, a precipitate of calcium carbonate is formed. It is preferable to separate this salt before the trialkylammonium acetate is extracted from the solution. Separation is accomplished by standard procedures such as filtration or centrifugation. When the process is used to recover acetic acid from a fermentation reaction, the calcium carbonate can be reused to maintain the pH of the fermentation medium in the desired range. By this procedure, the acetic acid produced in the fermentation reaction is converted to calcium acetate as it is produced by the microorganism.

The mixture of amine and acetic acid, which is present in the solution, is designated herein as a trialkylammonium acetate. This phrase includes the combination of amine and acetic acid in whatever form it occurs in solution. The combination may be a salt, a complex, or mixtures of these with the free amine and acetic acid.

In one embodiment of this invention, the trialkylammonium acetate is extracted from the solution by means of an organic solvent. Polar solvents, such as esters, alcohols, ketones, ethers or chlorinated hydrocarbons can be used. The solvents should be insoluble or sparingly soluble in water and be good extractants for the acetate. This extraction ability is determined by measuring the amount of acetic acid in each phase when an acetate solution is extracted with an equal volume of extractant. The extraction ability is expressed as a Distribution Coefficient ($K_D$) which is defined by the formula:

$$K_D = \frac{\text{grams acetic acid in organic phase/grams organic phase}}{\text{grams acetic acid in aqueous phase/grams aqueous phase}}$$

The solvent should have a $K_D$ greater than about 0.4 and preferably greater than about 1.

The organic solvent used in this invention should be one that does not react with the acetic acid under the conditions of the process. The solvent is preferably one having a boiling point sufficiently low so that it distills from a mixture of the solvent and acetate below the temperature at which the acetate evolves acetic acid. Furthermore, the solvent should not form an azeotrope with acetic acid. Chloroform is the preferred organic solvent for use in the process of this invention when the amine employed is tributylamine.

Methods other than solvent extraction can be used to concentrate the trialkylammonium acetate. These include evaporation of water from the acetate solution and freeze crystallization of the acetate.

In the final step of the process, the trialkylammonium acetate is heated to cause dissociation of the acetate with liberation of acetic acid and the amine. The temperature at which the acetate decomposes depends somewhat on the tertiary amine used. When tributylamine is employed, the acetate decomposes when held in a bath in the range of about 170°–190° C. with distillation of the acetic acid in a relatively pure form. The residue after distillation of the acid is tributylamine which can be recycled for use in the extraction process.

The procedure of this invention is further illustrated by the following examples in which all parts and percentages are by weight unless expressly stated to be otherwise.

EXAMPLE 1

Preparation of Tributylammonium Acetate

To a solution of 20 g of acetic acid and 400 ml of water was added 16 g of calcium carbonate. The resulting solution had a pH of 5.4. To this was added 62 g of tributylamine. Carbon dioxide was then introduced with shaking under 21.3 atmospheres pressure until the amine all dissolved and the pH dropped from 11 to 7. The precipitate was collected, washed with acetone and dried to give 15.4 g of 96% of the theoretical amount of calcium carbonate. Concentration of the filtrate under reduced pressure left a viscous syrup of tributylamine acetate.

EXAMPLE 2

Decomposition of Tributylammonium Acetate

The syrup obtained in Example 1 was placed in a flask fitted with a 7-cm Vigreux column attached to a water-cooled condenser. The flask was heated in an oil bath to 180° C. at which temperature decomposition of the acetate occurred. The yield of acetic acid distilling at 115°–118° C. was 18.3 g which represents a 91.5% recovery of the acetic acid present in the solution.

EXAMPLE 3

Preparation of Trialkylammonium Acetates

The procedure of Example 1 was followed except that the equivalent amounts of trimethylamine, triethylamine, tripropylamine, dicyclohexylmethylamine and 4-dimethylaminopyridine were used in place of tributylamine. In each case, over 90% of the theoretical amount of calcium carbonate precipitate was obtained and all of the amine went into solution. Under similar conditions, N,N-dimethyldodecylamine and N,N-dimethylhexadecylamine gave approximately 85% of the theoretical amount of calcium carbonate.

When triamylamine, trihexylamine and triisooctylamine were used in the process, the amine did not dissolve and no reaction appeared to take place.

EXAMPLE 4

Decomposition of Trialkylammonium Acetates

When the process of Example 2 was repeated with the syrups containing trimethylammonium acetate, triethylammonium acetate and tripropylammonium acetate, the products that were obtained were either azeotropes or mixtures of the tertiary amine and acetic acid. In contrast, when the procedure of Example 2 was applied to the syrup containing dicyclohexylmethylammonium acetate, the yield of the acetic acid fraction distilling at 112°–125° C. was 18.3 g, indicating that dicyclohexylmethylamine could be used like tributylamine. When salts were prepared from long-chain amines, such as dimethyldodecylamine, distillation was accompanied by unknown side-reactions which interfered with the recovery of pure acetic acid.

EXAMPLE 5

Extraction of Trialkylammonium Acetates

The efficiency with which trialkylammonium acetates could be extracted from water solutions with various solvents was measured by determination of the $K_D$ of the salts between water and the solvents according to the following procedure:

A mixture of 50 ml of a 5% aqueous solution of the acetate formed by the procedure of Example 1 and 50 ml of solvent in a 250-ml Erlenmeyer flask was shaken in a wrist-action shaker for 2 hours at room temperature. The mixture was transferred to a separatory funnel where it was allowed to stand for an additional hour before the phases were separated, weighed and analyzed. For analyses of the aqueous phase, a 1-ml sample was diluted with 15 ml of water and the resulting solution was titrated potentiometrically with 0.1 N NaOH solution. The organic phase was analyzed by diluting a 1-ml sample with 15 ml of methanol and titrating the solution potentiometrically with 0.1 N NaOH solution. The results of the analyses are reported as $K_D$ in Table I.

TABLE I

| | DISTRIBUTION COEFFICIENTS OF TRIALKYLAMMONIUM ACETATES | | | |
|---|---|---|---|---|
| | Distribution Coefficient ($K_D$) | | | |
| Solvent | Trimethyl-ammonium Acetate | Triethyl-ammonium Acetate | Tributyl-ammonium Acetate | Dicyclo-hexyl-methyl-ammonium Acetate |
| Chloroform | 0 | 0.043 | 1.7 | 0.39 |
| Trichloro-ethylene | 0 | 0.024 | 0.03 | 0.034 |
| 2-Ethyl Hexanol | 0 | 0.040 | 0.72 | 0.41 |
| Ethyl Acetate | 0 | 0.064 | 0.21 | 0.058 |
| Methyl Iso-butyl Ketone | 0 | 0.035 | 0.24 | 0 |

These results indicate that trimethylammonium acetate is too soluble in water to be extracted with the solvents tested. They also indicate that the extraction of tributylammonium acetate with chloroform is much more efficient than any of the other combinations.

EXAMPLE 6

Recovery of Acetic Acid From a Fermentation Broth

A fermentation broth containing 1.9% of acetic acid was obtained by fermentation of glucose with *Clostridium thermoaceticum* following the general procedure of Andreesen, et al., J. Bacteriology 114, 743 (1973). The acetic acid content of this broth was increased to 7.3% by the addition of acetic acid. The enriched broth was then neutralized to a pH of 5.3 by the addition of calcium carbonate. To 1 liter of the resulting solution, which contained 0.90 mole of acetic acid in the form of the calcium salt, was added 180 g (0.97 mole) of tributylamine. Carbon dioxide was added to the solution at a pressure of 1 to 2 atm. with shaking. The amine all dissolved and a precipitate of calcium carbonate formed. The solid was collected and found to weigh 46.3 g. The tributylammonium acetate was extracted from the solution using four 200-ml portions of chloroform. The combined chloroform extracts were dried over sodium sulfate and concentrated by distillation. The residual tributylammonium acetate was decomposed by the procedure given in Example 2. The main fraction of acetic acid boiling at 115°–118° C. was 45.3 g or 83.9% of the theoretical amount based on calcium acetate.

This experiment demonstrates that the procedure of this invention is suitable for the recovery of acetic acid from a fermentation broth in which the acetic acid is present in the form of calcium acetate.

Thus, it is apparent that there has been provided, in accordance with the invention, a process for the recovery of acetic acid from a solution in which the acid is in the form of its calcium salt that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

I claim:

1. A process for the recovery of acetic acid from an aqueous solution of clacium acetate which comprises the steps of:
   (a) adding a molar equivalent of a water-soluble tertiary amine carbonate to the calcium acetate solution to form a trialkylammonium acetate solution and a precipitate of calcium carbonate;
   (b) concentrating the trialkylammonium acetate solution; and
   (c) heating the concentrated trialkylammonium acetate solution to obtain acetic acid and the tertiary amine.

2. The process of claim 1 wherein the tertiary amine is tributylamine.

3. The process of claim 1 wherein the tertiary amine is dicyclohexylmethylamine.

4. The process of claim 1, 2 or 3 wherein the trialkylammonium acetate is concentrated by extraction with a solvent.

5. The process of claim 4 wherein the precipitated calcium carbonate is separated from the solution of trialkylammonium acetate before said acetate is extracted with a solvent.

6. The process of claim 4 wherein the solvent is chloroform.

7. The process of claim 4 wherein the solvent is distilled from the extract of trialkylammonium acetate before the acetate is heated to obtain acetic acid and the tertiary amine.

8. The process of claim 1 wherein the tertiary amine carbonate used in Step (a) is generated in situ by first adding to the calcium acetate solution a molar equivalent of a tertiary amine that forms a water-soluble carbonate and then adding sufficient carbon dioxide to dissolve the amine and to precipitate the calcium as calcium carbonate.

9. The process of claim 1 wherein the tertiary amine obtained in Step (c) is converted to a tertiary amine carbonate and recycled to Step (a).

10. A process for the recovery of acetic acid from a fermentation reaction which comprises:
  (a) converting of the acetic acid to calcium acetate;
  (b) adding a molar equivalent of a water-soluble tertiary amine carbonate to the calcium acetate solution to form a trialkylammonium acetate solution and a precipitate of calcium carbonate;
  (c) concentrating the trialkylammonium acetate solution; and
  (d) heating the concentrated trialkylammonium acetate solution to obtain acetic acid and the tertiary amine.

11. The process of claim 10 wherein the tertiary amine carbonate used in Step (b) is generated in situ by first adding to the calcium acetate solution a molar equivalent of a tertiary amine that forms a water-soluble carbonate and then adding sufficient carbon dioxide to dissolve the amine and to precipitate the calcium as calcium carbonate.

12. The process of claim 10 wherein the tertiary amine obtained in Step (d) is converted to a tertiary amine carbonate and recycled to Step (b).

13. The process of claim 10 wherein the calcium carbonate obtained in Step (b) is added to the fermentation reaction to convert the acetic acid to calcium acetate.

14. The process of claim 10 wherein the fermentation broth is one in which is grown a strain of *Clostridium thermoaceticum*.

15. The process of claim 10 wherein the tertiary amine is tributylamine.

16. The process of claim 10 wherein the tertiary amine is dicyclohexylmethylamine.

17. The process of claim 10, 15 or 16 wherein the trialkylammonium acetate is concentrated by extraction with a solvent.

18. The process of claim 17 wherein the solvent is distilled from the extract of trialkylammonium acetate before the acetate is heated to obtain acetic acid and the tertiary amine.

19. The process of claim 17 wherein the precipitated calcium carbonate is separated from the solution of trialkylammonium acetate before said acetate is extracted with a solvent.

20. The process of claim 17 wherein the solvent is chloroform.

* * * * *